United States Patent [19]

Sauer et al.

[11] Patent Number: 5,164,118
[45] Date of Patent: Nov. 17, 1992

[54] TERNARY SURFACTANT MIXTURES

[75] Inventors: Joe D. Sauer; Kim R. Smith; James E. Borland; Terry Crutcher, all of Baton Rouge, La.

[73] Assignee: Ethyl Corporation, Richmond, Va.

[21] Appl. No.: 787,239

[22] Filed: Nov. 4, 1991

[51] Int. Cl.$^5$ .................. B01J 17/00; B01F 17/22; B01F 17/28
[52] U.S. Cl. .................. 252/356; 252/357; 252/547; 252/DIG. 3; 252/DIG. 14
[58] Field of Search ............... 252/355, 353, 550, 554, 252/547, DIG. 3, DIG. 14, 357, 356

[56] References Cited

U.S. PATENT DOCUMENTS

| | | | |
|---|---|---|---|
| 4,271,030 | 6/1981 | Brierley et al. | 252/98 |
| 4,588,514 | 5/1986 | Jones et al. | 252/98 |
| 4,775,492 | 10/1988 | Vipond et al. | 252/187.26 |
| 4,789,495 | 12/1988 | Cahall et al. | 252/95 |
| 4,839,077 | 6/1989 | Cramer et al. | 252/98 |
| 4,938,953 | 7/1990 | Pena et al. | 424/70 |
| 5,034,150 | 7/1991 | Smith | 252/187.5 |
| 5,075,501 | 12/1991 | Borland et al. | 564/297 |
| 5,085,859 | 2/1992 | Halloran et al. | 424/71 |

Primary Examiner—Richard D. Lovering
Assistant Examiner—N. Bhat
Attorney, Agent, or Firm—Patricia J. Hogan

[57] ABSTRACT

Surfactant mixtures having improved foamability and/or cost performance consist of 5–90% by weight of an amine oxide corresponding to the formula RR'R"NO in which R is a primary alkyl group containing 6–24 carbons and R' and R" are independently selected from methyl, ethyl, and 2-hydroxyethyl, 5–90% by weight of an alkanolamide, and 5–60% by weight of an alkyl sarcosinate. Preferred mixtures are those in which the amine oxide is N-tetradecyldimethylamine oxide, the alkanolamide is cocodiethanolsuperamide, and the sarcosinate is sodium lauryl sarcosinate.

5 Claims, No Drawings

TERNARY SURFACTANT MIXTURES

FIELD OF INVENTION

This invention relates to surfactant compositions and more particularly to such compositions which are mixtures of amine oxides, alkanolamides, and sarcosinates.

BACKGROUND

It is known that various surfactants have been found to be useful in cleaning compositions, such as shower gels, shampoos, and light duty detergents (e.g., dish detergents)—compositions in which good foamability is a prerequisite for consumer approval. The surfactants which have been used to the greatest extent in such compositions are anionic surfactants, such as alkyl sufates, alkyl ether sulfates, sulfonates, sulfosuccinates, and sarcosinates.

Although the use of many of the anionic surfactants in these compositions permits the attainment of desirable characteristics, including good foamability, sarcosinates produce a relatively low level of foam. Moreover, they are particularly expensive to use. It would be beneficial to find a means of improving their foamability and/or the cost of using them.

SUMMARY OF INVENTION

It has been found that a mixture of 5-90% by weight of an amine oxide corresponding to the formula RR'R"NO in which R is a primary alkyl group containing 6-24 carbons and R' and R" are independently selected from methyl, ethyl, and 2-hydroxyethyl, 5-90% by weight of a fatty acid alkanolamide, and 5-60% by weight of an alkyl sarcosinate can provide better foamability and/or a better cost performance than any of the individual components of the mixture.

DETAILED DESCRIPTION

Amine oxides which can be used in the practice of the invention are compounds corresponding to the formula RR'R"NO in which R is a primary alkyl group containing 6-24 carbons, preferably 10-18 carbons, and R' and R" are independently selected from methyl, ethy, and 2-hydroxyethyl. The preferred amine oxides are those in which the primary alkyl group has a straight chain in at least most of the molecules, generally at least 70%, preferably at least 90% of the molecules; and the amine oxides which are especially preferred are those in which R contains 10-18 carbons and R' and R" are both methyl.

Exemplary of the preferred amine oxides are the N-hexyl-, N-octyl-, N-decyl-, N-dodecyl-, N-tetradecyl-, N-hexadecyl-, N-octadecyl-, N-eicosyl-, N-docosyl-, and N-tetracosyldimethylamine oxides, the corresponding amine oxides in which one or both of the methyl groups are replaced with ethyl or 2-hydroxyethyl groups, etc., and mixtures thereof. A particularly preferred amine oxide is N-tetradecyldimethylamine oxide.

Fatty acid alkanolamides which may be used in the mixtures are the known nonionic surfactants usually designated as superamides, i.e., alkanolamides obtained by reacting a fatty acid, usually a fatty acid containing 8-18 carbons, with an alkanolamine in equal proportions. The preferred alkanolamide is cocodiethanolsuperamide.

The alkyl sarcosinate employed in admixture with the amine oxide and alkanolamide may be any of the alkyl sarcosinates conventionally employed as surfactants. Such anionic surfactants are usually alkali metal or ammonium salts of alkyl sarcosinates in which the alkyl groups contain 8-18 carbons, and sodium lauryl sarcosinate is generally preferred.

Although the amounts of foam produced by the surfactant mixtures of the invention are not entirely dependent on maximizing their contents of the most foamable component, i.e., the amine oxide, and minimizing their contents of the leas foamable component, i.e., the sarcosinate, it is generally found that foamability is improved by increasing the amount of amine oxide in the mixture and maintaining the sarcosinate content at a level not higher than about 60%, preferably not more than about 50% by weight. The preferred mixtures contain about 10-90% by weight of the amine oxide, about 5-90% by weight of the alkanolamide, and about 5-50% by weight of the sarcosinate.

Among the more cost-effective mixtures are those containing the amine oxide, alkanolamide, and sarcosinate in weight ratios of 12/75/13, 75/12/13, 50/25/25, 34/33/33, and 25/50/25.

The invention is particularly advantageous in its provision of surfactant mixtures which provide acceptable levels of foam more economically than the individual components of the mixtures. This characteristic of the mixtures makes them valuable for use in the cleaning compositions which require foaming for customer approval, e.g., shampoos, shower gels, and light duty detergents.

When employed in such compositions, the surfactant mixtures are utilized in an aqueous medium, which typically constitutes about 10-90% of the weight of the compositions; and they may be used in conjunction with other ingredients of the types conventionally used in the compositions. Such ingredients, include, e.g., viscosity improvers, pH adjusters, colorants, pearlizing agents, clarifying agents, fragrances, preservatives, antioxidants, chelating agents, skin and hair conditioners, botanical extracts, and antibacterial agents.

The following example is given to illustrate the invention and is not intended as a limitation thereof. Unless otherwise specified, quantities mentioned in the example are quantities by weight.

EXAMPLE

Dissolve varying amounts of N-tetradecyldimethylamine oxide (AX), cocodiethanolsuperamide (SA), and sodium lauryl sarcosinate (SAR) in hard water (200 ppm as $CaCO_3$) to provide solutions having a total surfactant content of 0.1%. Measure the foamability of the surfactants by (1) placing 30 mL of each of the solutions in a 100 mL stoppered graduated cylinder, (2) inverting the cylinder ten times, (3) measuring the foam height, (4) repeating steps 1-3 twice, and (5) calculating the average of the three measurements. The proportions of amine oxide, alkanolamide, and sarcosinate used in preparing each of the solutions and the foam heights obtained from them are shown in the table below.

TABLE

| % AX | % SA | % SAR | Foam Height (mL) |
| --- | --- | --- | --- |
| 100 | 0 | 0 | 33 |
| 0 | 100 | 0 | 17 |
| 0 | 0 | 100 | 9 |
| 50 | 25 | 25 | 40 |
| 25 | 50 | 25 | 33 |
| 25 | 25 | 50 | 38 |

TABLE-continued

| % AX | % SA | % SAR | Foam Height (mL) |
|------|------|-------|------------------|
| 75   | 12   | 13    | 44               |
| 12   | 75   | 13    | 36               |
| 12   | 13   | 75    | 30               |
| 34   | 33   | 33    | 40               |

What is claimed is:

1. A surfactant mixture consisting of 5-90% by weight of an amine oxide corresponding to the formula RR'R"NO in which R is a primary alkyl group containing 6-24 carbons and R' and R" are independently selected from the group consisting of methyl, ethyl, and 2-hydroxyethyl, 5-90% by weight of a superamide fatty acid alkanolamide, and 5-60% by weight of an alkyl sarcosinate surfactant.

2. The surfactant mixture of claim 1 wherein R is a primary alkyl group containing 10-18 carbons, R' and R" are methyl, and the alkanolamide and sarcosinate contain alkyl groups of 8-18 carbons.

3. The surfactant mixture of claim 2 wherein the amine oxide is N-tetradecydimethylamine oxide, the alkanolamide is cocodiethanolsuperamide, and the sarcosinate is sodium lauryl sarcosinate.

4. The surfactant mixture of claim 1 containing 10-90% by weight of the amine oxide, 5-90% by weight of the alkanolamide, and 5-50% by weight of the sarcosinate.

5. The surfactant mixture of claim 4 wherein the amine oxide is N-tetradecyldimethylamine oxide, the alkanolamide is cocodiethanolsuperamide, and the sarcosinate is sodium lauryl sarcosinate.

* * * * *